(12) United States Patent
Biron et al.

(10) Patent No.: US 7,837,848 B2
(45) Date of Patent: Nov. 23, 2010

(54) BIDIMENSIONAL SEPARATION BY MEANS OF CAPILLARY ELECTROPHORESIS CARRIED OUT IN A SINGLE CAPILLARY

(75) Inventors: Jean-Philippe Biron, Saint Gely du Fesc (FR); Hervé Cottet, Montpellier (FR)

(73) Assignees: Centre National de la Recherche Scientifique (C.N.R.S.), Paris (FR); Universite de Montpellier II, Montpellier (FR)

( * ) Notice: Subject to any disclaimer, the term of this patent is extended or adjusted under 35 U.S.C. 154(b) by 1124 days.

(21) Appl. No.: 10/569,632

(22) PCT Filed: Aug. 23, 2004

(86) PCT No.: PCT/FR2004/002181

§ 371 (c)(1),
(2), (4) Date: Feb. 27, 2006

(87) PCT Pub. No.: WO2005/024410

PCT Pub. Date: Mar. 17, 2005

(65) Prior Publication Data

US 2006/0254914 A1    Nov. 16, 2006

(30) Foreign Application Priority Data

Aug. 29, 2003   (FR)   ................................... 03 10299

(51) Int. Cl.
*G01N 27/447* (2006.01)
*G01N 27/453* (2006.01)

(52) U.S. Cl. ........................ 204/451; 204/452; 204/453; 204/454; 204/600; 204/601

(58) Field of Classification Search ................. 204/451, 204/454, 452, 453
See application file for complete search history.

(56) References Cited

U.S. PATENT DOCUMENTS 5,089,111  A  *  2/1992   Zhu et al.   .................... 204/451

(Continued)

FOREIGN PATENT DOCUMENTS

JP           58021553  A  *  2/1983

(Continued)

OTHER PUBLICATIONS

D. Corradini, "Buffer Additives Other Than The Surfactant Sodium Dodecyl Sulfate For Protein Separations By Capillary Electrophoresis" Journal of Chromatography B 699, p. 221-256 (1997).*

(Continued)

*Primary Examiner*—Harry D Wilkins, III
*Assistant Examiner*—Bryan D. Ripa
(74) *Attorney, Agent, or Firm*—Young & Thompson

(57) ABSTRACT

A method for separating the constituents of a mixture M by electrophoresis in a single capillary includes (A) separating compounds of the mixture M in a single capillary according to the capillary electrophoresis technique; (B) isolating a fraction F of the compounds thus separated by evacuating part of the compounds having the highest migration speeds from the capillary and/or evacuating part of the compounds having the lowest migration speeds from the capillary; (C) introducing a separating medium MS having a higher migration speed than the compounds of the isolated fraction F into the capillary containing the isolated fraction F, and (D) the compounds contained in fraction F are separated in the new electrophoretic conditions thus obtained.

25 Claims, 2 Drawing Sheets

U.S. PATENT DOCUMENTS

| | | | | |
|---|---|---|---|---|
| 5,196,039 | A | * | 3/1993 | Phillips et al. ............... 210/656 |
| 5,415,747 | A | * | 5/1995 | Holloway ................... 204/453 |
| 5,798,032 | A | * | 8/1998 | Khan et al. ................. 204/452 |
| 5,916,426 | A | * | 6/1999 | Madabhushi et al. ........ 204/451 |
| 6,090,250 | A | * | 7/2000 | Mazzeo et al. .............. 204/451 |
| 6,537,432 | B1 | * | 3/2003 | Schneider et al. ........... 204/450 |
| 2002/0098595 | A1 | * | 7/2002 | Lubman et al. .............. 436/178 |
| 2002/0130045 | A1 | * | 9/2002 | Schlenoff et al. ........... 204/454 |

FOREIGN PATENT DOCUMENTS

| | | |
|---|---|---|
| WO | WO 03/015901 | 2/2003 |

OTHER PUBLICATIONS

English Translation of JP 58-21553A.*

N.J. Reinhoud et al., "Automated Isotachophoretic Analyte Focusing For Capillary Zone Electrophoresis in A Single Capillary Using Hydrodynamic Back-Pressure Programming" Journal of Chromatography 641, p. 155-162 (1993).*

Patent Abstracts of Japan vol. 007, No. 096 (P-193), Apr. 22, 1983 & JP 58 021553 A (Shimazu Seisakusho KK), Feb. 8, 1983 abstract.

N.J. Reinhoud et al: "automated isotachophoretic analyte focusing for capillary zone electrophoresis in a single capillary using hydrodynamic back-pressure programming" Journal of Chromatography, vol. 641, 1993, pp. 155-162, XP008028909, p. 156, right-hand column, last paragraph-p. 157.

Patent Abstracts of Japan vol. 007, No. 096 (P-193), Apr. 22, 1983 & JP 58 021552 A (Shimazu Seisakusho KK), Feb. 8, 1983 abstract.

* cited by examiner

BIDIMENSIONAL SEPARATION BY MEANS OF CAPILLARY ELECTROPHORESIS CARRIED OUT IN A SINGLE CAPILLARY

BACKGROUND OF THE INVENTION

1. Field of the Invention

The present invention relates to a method for two-dimensional separation of the constituents of a mixture, using a capillary electrophoresis technique, carried out in a capillary or an equivalent system such as a microchip-type system. This method, especially adapted to the separation of mixtures of electrically charged polymers (synthetic or natural), such as mixtures of proteins or of peptides, is for example useful for analyzing the constituents of such mixtures.

2. Description of the Related Art

"Two-dimensional" separation techniques consist in carrying out the separation of the constituents of a mixture according to two distinct successive criteria. Thus, these methods generally implement a first step which consists in separating the constituents of the mixture under first separation conditions, and then a second step consisting in subjecting all or some of the separated fractions obtained at the end of the first step to a further separation under new conditions. The two successive separation steps used in these methods generally implement two separations of different types, based on two distinct characteristics of the constituents to be separated. These two successive separation steps are referred to as "orthogonal" with respect to one another.

The term "two-dimensional separation" comes from the fact that, originally, this type of separation denotes a separation carried out on supports actually having two dimensions, such as plates. Thus, for example, two-dimensional chromatography consists in loading a sample of mixture onto a plate, in carrying out an elution of the mixture by means of a first eluent in a first direction of the plate, and then in eluting each of the separated fractions of the mixture (aligned according to the first direction) using a second eluent in a direction which is orthogonal to the first direction, whereby a separation of the constituents in the two dimensions of the plate is obtained. Similarly, two-dimensional electrophoresis techniques on a gel layer have been developed, comprising a first electrophoretic separation of the compounds of a mixture by migration according to a first direction of the gel, followed by a second migration in an orthogonal direction, under other electrophoresis conditions. These techniques are widely used, especially in the field of the separation and analysis of mixtures of proteins. In this case, two-dimensional electrophoresis techniques on gel, called (IEF/SDS-PAGE), have in particular been developed, which are suitable for the separation of proteins or peptides, and in which the first separation is carried out by isoelectric focusing (IEF), which allows separation according to the isoelectric point in a first direction of the gel, and the second step consists of electrophoretic migration in an orthogonal direction, carried out in the presence of a polyacrylamide gel and sodium dodecyl sulfate (SDS-PAGE). For further information concerning two-dimensional electrophoresis techniques, and in particular techniques of the (IEF/SDS-PAGE) type, reference may in particular be made to the article by P. A. Haynes, S. P. Gygi, D. Figeys, R. Aebersold, in *Electrophoresis*, 19, 1862-1871 (1998).

By extension, the term "two-dimensional" separation has subsequently been extended to any method using two successive steps of one-dimensional separation, in which the second step consists in separating the compounds of at least one of the fractions separated during the first step. By analogy with the techniques on a two-dimensional support, the second separation step is referred as being carried out "according to an orthogonal direction", even when no two-dimensional support is concretely used.

Various two-dimensional separation techniques are currently known, which couple two (or more) successive "one-dimensional" separation steps, such as chromatography or electrophoresis steps. By way of examples of two-dimensional separation techniques of this type, mention may in particular be made of the techniques described in the work *High Performance Capillary Electrophoresis, Chemical Analysis Series*, vol. 146, No. 17, 581-612 (1998) or those described by J. M. Hille, A. L. Freed, and H. Watzig, in *Electrophoresis*, 22, 4035-4052 (2001).

Especially, two-dimensional separation techniques using at least one step of capillary electrophoresis in their separation steps have been developed. In this context, certain authors have in particular described the coupling of two successive capillary electrophoresis steps. In this respect, reference may e.g. be made to the articles by Mark R. Shure in *Anal. Chem.* 71, 1645-1657 (1999), or by Deepa Mohan and Cheng S. Lee in *Electrophoresis* 23, 3160-3167 (2002).

These two-dimensional separation methods appear, a priori, to be attractive, especially since they seem to be capable of combining the advantages of two-dimensional separation with the particularly marked effectiveness of electrophoretic separation. However, in practice, these methods generally require the use of complex and most commonly expensive devices, and the separation carried out is not always up to the quality expected.

Especially, techniques using two successive steps of capillary electrophoresis currently consist in coupling two capillaries, so as to be able to carry out the two electrophoreses in distinct media. This coupling of two capillaries is generally difficult to carry out, and it requires coupling devices which are often expensive.

Furthermore, as underlined in particular by Shure et al., in Anal. Chem 71, 1645-1657 (1999), the use of these coupling devices generally affects the quality of the separation produced, resulting in particular in phenomena of peak broadening which can be limited only with great difficulty. Furthermore, the coupling of two capillaries most commonly involves sampling steps, during which part of the compounds to be analyzed can be lost, or involves dilution processes which prove in particular to be prejudicial in terms of the sensitivity of detection of the compounds separated, most particularly when the initial mixture to be analyzed is a dilute medium.

Thus, the techniques of two-dimensional separation by coupling of two successive capillary electrophoresis steps that are currently known prove to be unsatisfactory in terms of effectiveness and/or of cost. Given these drawbacks, this type of two-dimensional separation is very rarely used in practice.

SUMMARY OF THE INVENTION

However, against all expectation, the inventors have now discovered that it is possible to carry out a two-dimensional separation using two successive capillary electrophoresis steps in a particularly simple and effective manner, by using a single capillary for the two electrophoresis steps, which makes it possible in particular to do away with the technical problems and/or problems of expense associated with the use of the systems of capillary/capillary coupling currently employed.

More specifically, the inventors' studies have made it possible to establish that if, after a separation by electrophoresis carried out in a capillary a fraction of the separated compounds is isolated in the capillary used, it is subsequently possible, without using an additional capillary, to carry out a further separation of the isolated fraction by electrophoresis, by injecting into the capillary a separating medium having a faster migration speed than the isolated fraction in the capillary.

It was also found that the separation thus carried out is particularly effective and that, in most cases, the separation can be obtained without observing the phenomena of peak broadening which are generally obtained in the case of currently known separation methods which couple two capillary electrophoresis steps.

On the basis of these discoveries, one aim of the present invention is to provide a method of two-dimensional separation using two successive capillary electrophoresis steps, which is both effective and relatively inexpensive. In this context, the invention especially aims at providing a method of two-dimensional separation by capillary electrophoresis, which does away with the drawbacks associated with the use of the systems of capillary/capillary coupling used in the two-dimensional capillary electrophoresis techniques currently known.

To this end, according to a first aspect, a subject of the invention is a method for separating the constituents of a mixture M comprising electrically charged compounds, by capillary electrophoresis in a single capillary, said method comprising the steps consisting in:

(A) introducing and migrating the compounds of the mixture M in the capillary according to the capillary electrophoresis technique (i.e. under the effect of a potential difference applied between the inlet and the outlet of the capillary), so as to produce a separation of the compounds of the mixture M in the capillary, according to their migration speed under the conditions of step (A);

(B) isolating in the capillary a fraction F of the compounds separated in step (A), by carrying out one and/or the other of the following steps:

(B.1) evacuating out of the capillary a part of the compounds having the fastest migration speeds under the electrophoresis conditions of step (A), by allowing these compounds to migrate at the outlet of the capillary, most commonly by maintaining the potential difference of step (A); and/or (B.2) evacuating out of the capillary a part of the compounds having the slowest migration speeds under the electrophoresis conditions of step (A), by migrating these compounds toward the inlet of the capillary, in general by applying an overpressure at the outlet of the capillary and/or by applying between the inlet and the outlet of the capillary a potential difference of opposite polarity to that of step (A), this step (B) optionally being followed by a step (B') consisting in optionally migrating the isolated fraction F toward the inlet of the column; and (C) under the effect of a potential difference applied between the inlet and the outlet of the capillary (which induces an electroosmotic flow), introducing, into the capillary containing the isolated fraction F, a separating medium MS having a migration speed greater than that of the compounds of the fraction F, such that said separating medium catches up with the isolated fraction F in the capillary, and thus modifies the environment of the fraction F and, consequently, the electrophoresis conditions for this fraction, and maintaining the potential difference until there is separation of the compounds included in the isolated fraction as a function of their migration speed under the new electrophoresis conditions obtained.

Thus, the method of the invention is a method for two-dimensional separation of the compounds of the mixture M, that makes it possible to carry out a first separation of the constituents of the mixture M by capillary electrophoresis ("first dimension" of step (A)), followed by a second separation of the constituents of a fraction of the compounds thus separated ("second dimension" of step (C)). Characteristically, in the method of the invention, these two successive separations are carried out in the same single capillary, which is made possible by the isolation step (B).

The term "single capillary" as used in the present description denotes most commonly a capillary as used in the conventional capillary electrophoresis technique, but it can also denote systems equivalent to such capillaries, such as the "microchip"-type systems described, for example, in *Microfabricated capillary electrophoresis amino acid chirality analyser for extraterrestrial exploration*, Hutt, L. D., Glavin, D. P., Bada, J. L., Mathies, R. A., Anal. Chem. 1999, 71, 4000-4006. Although the present description especially refers to a capillary electrophoresis carried out in a conventional capillary system, it is understood that the principles stated for this type of electrophoresis are entirely transposable to the use of similar systems, such as "microchip" systems.

The mixture M, the constituents of which are separated according to the method of the invention, can be any mixture of electrically charged compounds which is suitable for separation by capillary electrophoresis. For further specifications concerning the mixtures that can be separated by capillary electrophoresis, reference may in particular be made to the article by M. G. Khaledi in *High Performance Capillary Electrophoresis, Chemical Analysis Series*, vol. 146, (1998), or else to the work by S. F. Y. Li "*Capillary electrophoresis: principles, practice and applications*", *Journal of Chromatography Library*, vol. 52, third edition (1996).

In general, the mixture M is a mixture of several charged compounds of the same charge. Thus, according to a first embodiment, the mixture M is a mixture of negatively charged species, such as, for example, a mixture comprising synthetic polymers carrying anionic groups and/or negative charges, proteins and/or peptides at a pH sufficiently high for them to carry negative charges, negatively charged polysaccharides, and/or anionic molecules (for example, acids in deprotonated form, in particular deprotonated organic acids). According to another embodiment, the mixture M is a mixture of positively charged species, comprising, for example, positively charged synthetic polymers carrying cationic groups and/or positive charges, proteins and/or peptides at a pH sufficiently low for them to carry positive charges, positively charged polysaccharides, or cationic molecules (for example, bases in protonated form, and in particular protonated organic bases).

In the abovementioned capillary electrophoresis steps (A) and (C), it is most commonly preferred for the charged species to be separated to migrate in the capillary with electroosmotic counterflow. To this end, the internal surface of the capillary used is preferably coated with charges of the same sign as those of the charged species to be separated in the mixture M.

Thus, when the mixture M is a mixture of negatively charged species, the capillary used is advantageously a capillary whose internal surface carries negative charges. Thus, it may be a capillary having an internal wall of virgin silica (which is negatively charged in an aqueous medium with a pH of greater than 2), it being possible for this wall to be optionally covered with anionic protective groups (for example, sulfonate groups), or else with several layers of polyelectrolytes, with a final layer (in contact with the internal medium of the capillary) based on an anionic polyelectrolyte, such as, for example, a dextran sulfate. Such a modification of the surface of a silica capillary with multilayers of polyelectrolytes is described in particular by H. Katayama, Y. Ishihama et al., in *Anal. Chem.*, 70, 2254-2260 (1998). The use of silica capillaries with a modified internal surface of the abovementioned types proves to be in particular advantageous when all or part of the compounds of the mixture M are capable of interacting with silica, and in particular of binding to the silanol-type groups presented by a wall of silica.

When the mixture M is a mixture of positively charged species, the capillary used is advantageously a capillary whose internal surface carries positive charges, such as a silica capillary grafted with quaternary ammonium groups, or covered with multilayers of polyelectrolytes, the final layer of which is a cationic polyelectrolyte such as, for example, polybrene.

More generally, step (A) of the method of the invention is a step consisting of separation by conventional capillary electrophoresis, which is advantageously carried out so as to separate as much as possible the constituents of the mixture M, in general according to their charge or according to their charge/mass ratio. It is within the competence of a specialist in electrophoresis to adjust the conditions to be used so as to obtain as effective a separation as possible in step (A). For further details concerning the general conditions for performing an electrophoresis carried out so as to separate a mixture of compounds according to their charge or according to their charge/mass ratio, reference may in particular be made to the article by M. G. Khaledi in *High Performance Capillary Electrophoresis, Chemical Analysis Series*, vol. 146, (1998), or to the abovementioned work by S. F. Y. Li "Capillary electrophoresis: principles, practice and applications", *Journal of Chromatography Library*, vol. 52, third edition (1996).

After the electrophoresis of step (A), separation of the compounds of the mixture into several fractions is generally obtained, each of these fractions comprising the compounds having a given migration speed under the conditions of step (A). Each of these fractions appears in the form of a single peak on an electropherogram. However, in particular in the case of complex mixtures such as mixtures of proteins, each of the peaks observed often contains a mixture of several constituents.

The fraction F isolated in step (B) is a mixture of compounds having migration speeds between two cutoff values $V_{min}$ and $V_{max}$ (with $V_{min}<V_{max}$) under the electrophoresis conditions of step (A). Step (B.1), when it is carried out, consists in evacuating from the capillary the compounds having migration speeds greater than $V_{max}$. Similarly, step (B.2), when it is carried out, consists in evacuating from the capillary the compounds having migration speeds greater than $V_{min}$.

Most commonly, the fraction F isolated in step (B) is a mixture of compounds having substantially the same migration speed under the electrophoresis conditions of step (A), i.e. a fraction consisting of the compounds corresponding to one of the electrophoretic peaks obtained following the electrophoresis of step (A). Step (B) then consists in evacuating from the capillary the compounds having a different migration speed, corresponding to the other peaks of the electropherogram, and step (C) consists in carrying out a separation of the constituents of the mixture of compounds corresponding to the isolated peak in the capillary. The isolation of a fraction F consisting of the compounds corresponding to a single electrophoretic peak often proves to be advantageous, in particular in so far as it has the advantage of preventing any phenomenon of peak overlap during the electrophoretic separation of step (C).

However, according to one embodiment that can be envisioned, the fraction F isolated in step (B) can also be a mixture of compounds corresponding to a series of successive electrophoretic peaks obtained following the electrophoresis of step (A). In this case, step (B) consists in evacuating from the capillary the compounds corresponding to the peaks of the electropherogram that are located before and/or after the series of peaks to be isolated.

Depending on the fraction F that it is desired to isolate in step (B), three major embodiments can be envisioned for step (B).

Thus, according to a first embodiment of the method of the invention, the fraction F is a head fraction, i.e. a fraction consisting of a mixture of compounds having one or more migration speed(s) greater than that of the compounds that are migrated from the capillary. In this case, step (B) consists in carrying out only step (B.2), without carrying out step (B.1).

According to this first embodiment, the fraction F isolated in step (B) advantageously consists of the compounds of the head peak that can be observed on an electropherogram of the electrophoresis of step (A), i.e. a mixture of the compounds having the fastest migration speed ($V_{head}$) under the electrophoresis conditions of step (A), which thus appear first on an electropherogram of the electrophoresis of step (A). In this case, step (B.2) consists in removing out of the capillary the compounds other than the compounds of the head peak, which have a migration speed less than $V_{head}$.

Alternatively, the head fraction isolated in step (B) can consist of the compounds of two or more of the first peaks that appear on an electropherogram of the electrophoresis of step (A). In this case, step (B.2) consists in removing out of the capillary the compounds corresponding to the other peaks.

To isolate a head fraction, regardless of its nature (compounds corresponding to a single electrophoretic peak or to several peaks), step (B.2) can advantageously consist in applying an overpressure at the outlet of the capillary, until the compounds that are not part of the head fraction F to be isolated are made to exit via the inlet of the capillary.

For the purpose of the description and of the claims, the expression "application of an overpressure at the outlet of the capillary" is intended to mean the application of a positive pressure difference between the outlet and the inlet of the capillary. In practice, this positive pressure difference is generally induced by applying an overpressure at the outlet of the capillary. However, according to certain specific embodiments, this pressure difference can also be induced by applying a low pressure at the inlet of the capillary, optionally in combination with an overpressure at the outlet of the capillary. The "overpressure at the outlet of the capillary" to which reference is made in the present document denotes in general the positive pressure difference applied between the outlet and the inlet of the capillary.

When an overpressure is applied at the outlet of the capillary, the diameter of the capillary used is advantageously less than 50 microns, and more preferably less than or equal to 30 microns, and even more advantageously less than or equal to 20 microns, and the overpressure imposed at the outlet of the capillary is preferably as small as possible, especially so as to prevent phenomena of dispersion, which would result in a broadening of the peaks observed on an electropherogram, which would harm the quality of the separation obtained. Thus, it is generally preferred that the overpressure imposed in step (B) be an overpressure of less than 100 millibar, and preferably less than 80 millibar, advantageously less than 1 psi (less than 69 millibar) [indicative values, explained hereinafter]. Most commonly, the limiting value of the overpressure that can be imposed without observing too great a peak broadening is to be adjusted according to the internal diameter of the capillary used. Thus, the finer the capillary, the greater the overpressure that may be imposed. By way of example, for a capillary with an internal diameter of less than 20 microns (10 microns, for example), it is possible to envision imposing an overpressure ranging up to 100 millibar, or even up to 2 psi (138 millibar) without observing dispersion phenomena that are too marked. On the other hand, for capillaries with an internal diameter of between 20 and 30 microns (typically 25 microns), it is preferable not to exceed an overpressure of 1 psi (69 millibar). For capillaries with an internal diameter of greater than 30 microns, the overpressure that can be envisioned without observing troublesome dispersion phenomena is preferably less than 0.5 psi, and even more advantageously less than 0.2 psi. For an internal diameter of 50 microns, it is preferable not to exceed 0.1 psi.

Alternatively, in certain cases, step (B.2) carried out in order to isolate a head fraction can also consist in:
  (i) applying, between the inlet and the outlet of the capillary, a potential difference of opposite polarity to that of step (A), taking care not to recombine the fraction F to be isolated with the other compounds separated from the mixture M; then
  (ii) applying an overpressure at the outlet of the capillary until the compounds that are not part of the head fraction F to be isolated are made to exit via the inlet of the capillary, most commonly maintaining the potential difference of step (i).

The use of the abovementioned steps (i) and (ii) for carrying out step (B.2) makes it especially possible to limit the peak broadening phenomena which can be observed when (B.2) consists only in applying an overpressure at the outlet of the capillary.

When it is used, step (i) is carried out for a sufficiently short period so as not to lead to a recombination of the head peak(s) to be isolated, with the peaks that it is desired to remove from the capillary. When the fraction F to be isolated does not consist of a single head peak, but of several, step (i) is also advantageously carried out for a sufficiently short period of time so as not to observe any recombination of the peaks of the fraction F to be isolated. In practice, the potential difference applied between the outlet and the inlet of the capillary in step (i) is in general the same potential difference (in absolute value) as that applied in step (A), but with an opposite sign. In other words, step (i) is advantageously carried out by reversing the polarity at the limits of the capillary, with respect to step (A). In particular in this case, the amount of time for which step (i) is carried out can be readily determined by means of an electropherogram of the electrophoresis of step (A), which provides the migration speed of each of the compounds and the spacing between the various peaks. These two parameters make it possible to calculate the space between two peaks after the polarity has been reversed for a given period of time.

Preferably, when it is used, step (i) is preferably carried out such that the spacing between the fraction F to be isolated and the other peaks to be eliminated is at least 5 mm, and preferably at least 10 mm in the capillary.

When the succession of steps (i) and (ii) is used as step (B.2) for isolating a head fraction F, the overpressure imposed in step (ii) at the outlet of the capillary is preferably an overpressure of less than 100 millibar, this overpressure being advantageously less than 80 millibar, and advantageously less than 1 psi (69 millibar), in particular when the capillary used has an internal diameter of between 20 and 50 microns. Here again, the limiting value of the overpressure that can be imposed depends on the internal diameter of the capillary used.

According to a second embodiment of the method of the invention, step (B) consists in carrying out step (B.1) so as to evacuate a head fraction, and then step (B.2) so as to evacuate a tail fraction, and the fraction F isolated in step (B) is then a core fraction.

According to this second embodiment, the core fraction F isolated advantageously consists of the compounds of one of the peaks between the tail peak and the head peak that can be observed on an electropherogram of the electrophoresis of step (A), i.e. a mixture of the compounds having the same migration speed V under the electrophoresis conditions of step (A), which is intermediate between the speed of the head compounds ($V_{head}$) and the speed of the tail compounds ($V_{tail}$). In this case, step (B.1) consists in causing all the compounds having a migration speed greater than V to exit the capillary, and step (B.2) consists in causing all the compounds having a migration speed less than V to exit the capillary.

Alternatively, according to this second embodiment, the core fraction F isolated in step (B) can consist of the compounds of two or more intermediate peaks between the tail peak and the head peak, i.e. a mixture of the compounds having migration speeds between a value V' greater than $V_{tail}$ and a value V" greater than V' and less than $V_{head}$ under the electrophoresis conditions of step (A). Where appropriate, step (B.1) consists in causing all the compounds having a migration speed greater than V" to exit the capillary, and step (B.2) consists in causing all the compounds having a migration speed of less than V' to exit the capillary.

Thus, the isolation of a core fraction involves a first step (B.1) which consists in eliminating a head fraction, as a result of which the fraction F to be isolated becomes the head fraction in the capillary. From then on, the isolation of this fraction F amounts to isolating a head fraction according to step (B.2), as in the first embodiment of the method. Thus, in order to isolate a core fraction, step (B.2) carried out subsequent to step (B.1) is advantageously to be carried out under the conditions of the first embodiment of the method.

Thus, step (B.2) used in the context of the isolation of a core fraction preferably consists in:
  according to a first possibility: applying an overpressure at the outlet of the capillary, preferably within the advantageous ranges indicated for the first embodiment of the method, until the compounds that are not part of the head fraction F to be isolated, i.e. the compounds having a migration speed less than V' under the electrophoresis conditions of step (A), are made to exit via the inlet of the capillary; or
  according to a second possibility, adjusted in particular so as to limit the peak broadening phenomena:
    (i) applying, between the inlet and the outlet of the capillary, a potential difference of opposite polarity to that of step (A), taking care not to recombine the fraction F to be isolated with the other compounds separated from the mixture M; then
    (ii) applying an overpressure at the outlet of the capillary, preferably within the advantageous ranges indicated for the first embodiment of the method, until the compounds that are not part of the head fraction F to be isolated, i.e. the compounds having a migration speed less than V' under the electrophoresis conditions of step (A), are made to exit via the inlet of the capillary.

According to a third embodiment of the method of the invention, the fraction F isolated in step (B) of the method is a tail fraction, i.e. a fraction consisting of a mixture of compounds having one (or more) migration speed(s) less than that of the compounds which are made to migrate out of the capillary. In this case, step (B) consists in carrying out only step (B.1), without carrying out step (B.2).

According to this first embodiment, the fraction F isolated in step (B) advantageously consists of the compounds of the tail peak that can be observed on an electropherogram of the electrophoresis of step (A), i.e. a mixture of the compounds having the slowest migration speed ($V_{tail}$) under the electrophoresis conditions of step (A), which therefore exit last on an electropherogram of the electrophoresis of step (A). In this case, step (B.1) consists in causing the compounds other than the compounds of the tail peak, i.e. all the compounds which have a migration speed greater than $V_{head}$, to exit the capillary.

Alternatively, the head fraction isolated in step (B) can consist of the compounds of two or more of the final peaks appearing on an electropherogram of the electrophoresis of step (A). Where appropriate, step (B.1) consists in causing the compounds corresponding to the other peaks to exit the capillary.

When step (B) consists in isolating a tail fraction in the capillary, the isolated tail fraction F obtained at the end of step (B.1) is generally located toward the outlet of the capillary, and this is most commonly found to be advantageous, in particular so as to be able to perform an effective separation in step (C), to migrate the compounds of the fraction F toward the inlet of the capillary.

More generally, it is often advantageous, prior to the introduction of the separating medium of step (C), to migrate the isolated fraction F in the capillary in the direction of the inlet of the capillary, preferably in such a way that the isolated fraction is located in the first tenth of the capillary, preferably in the first twentieth of the capillary, and typically in such a way that the isolated fraction is located at a distance from the inlet of the capillary of between 0.5 and 2 cm, and preferably at a distance of the order of 1 cm. In other words, it is generally preferred, in the method of the invention, for step (B') to be carried out.

Preferably, when step (B') is carried out, the migration of the isolated fraction F in the capillary toward the inlet of the capillary is induced by applying an overpressure at the outlet of the capillary, in particular when step (B.2) is carried out. In fact, when step (B.2) and step (B') are carried out, these two steps are generally combined into one and the same step consisting in migrating the fraction F to be isolated such that it is as close as possible to the inlet of the capillary (preferably in the first tenth of the capillary, and advantageously in the first twentieth), as a result of which is obtained, de facto, an elimination of the compounds having a migration speed less than that of the fraction F, via the inlet of the capillary.

Alternatively, according to another variant of step (B') that can be envisioned, and that is in particular suitable when step (B) consists only in carrying out step (B.1), the migration of the isolated fraction F in the capillary toward the inlet of the capillary can be induced by applying, between the inlet and the outlet of the capillary, a potential difference of opposite polarity to that of step (A). This migration has in particular the advantage of avoiding any possibility of phenomena of broadening of the peak(s) of the fraction F such as those observed when there is a hydrodynamic flow induced by the application of an overpressure at the outlet of the capillary.

When step (B') is carried out, it is essential for the migration of the fraction F toward the inlet of the capillary to be stopped before the fraction F exits the capillary. This is because the aim of steps (B) and (B') is to isolate the fraction F in the capillary. In order to prevent the fraction F to be isolated exiting into the outside medium, it can be advantageous to have a detector at the inlet of the capillary (or close to the inlet of the capillary, typically at a distance of 1 to 10 cm from the inlet), that makes it possible to control, firstly, the leaving of the various fractions to be eliminated via the inlet of the capillary and, secondly, the maintaining of the fraction F to be conserved in the capillary.

In general, it is indicated that the capillary similarly has a detector before the outlet of the capillary, that makes it possible to control the elimination of the various fractions to be eliminated via the outlet of the capillary and the maintenance of the fraction F to be conserved in the capillary. In this case, most of the usual capillary electrophoresis devices can be used to carry out the method of the invention. For example, the method of the invention can advantageously be carried out in a capillary electrophoresis device of the 3DCE type sold by Agilent Technologie or else a device of the PACE MDQ type sold by Beckman Coulter.

Moreover, more generally, the capillary used in steps (A) to (C) is advantageously a capillary having an internal diameter of between 5 and 100 microns. In particular so as to be able to carry out steps (B2) and (B') in an optimal manner, this internal diameter is advantageously less than or equal to 50 microns, preferably less than or equal to 40 microns, and advantageously less than or equal to 30 microns, or even, in certain cases, less than 20 microns. It is, however, preferable for this internal diameter to remain greater than or equal to 10 microns, or even to 15 microns, in particular so as not to decrease too greatly the sensitivity of the detection at the capillary outlet.

Thus, as a capillary that can advantageously be used to carry out the separation method according to the invention, mention may in particular be made of capillaries having an internal diameter of between 10 and 50 microns, such as the usual capillaries having an internal diameter equal to 10 microns, 25 microns or to 50 microns, 25-micron capillaries proving in particular to be very suitable in most cases.

Moreover, in particular so as to optimize the quality of the separation in steps (A) and (C), a capillary used for the method of the invention is preferably a capillary with as short a length as possible, preferably less than 1 m, and advantageously less than 50 cm. In general, and in particular when step (B.2) is carried out, it is preferable for the length of the capillary to remain less than or equal to 40 cm, this length being advantageously less than or equal to 35 cm, in particular so as to make it possible to carry out step (B.2) without observing any peak broadening phenomena that are too marked. Thus, typically, the length of a capillary used in steps (A) to (C) of the method of the invention is advantageously between 20 and 60 cm, preferably between 20 and 40 cm (typically, of the order of 30 to 35 cm).

As indicated above in the description, it is also possible to envision using systems of the "microchip" type as capillaries for carrying out the method of the invention. Where appropriate, these systems may, for example, be selected from the systems described in *Microfabricated capillary electrophoresis amino acid chirality analyser for extraterrestrial exploration*, Hutt, L. D., Glavin, D. P., Bada, J. L., Mathies, R. A., Anal. Chem. 1999, 71, 4000-4006 or those used in devices such as those sold under the name "Agilent 2100 Bioanalyseur" by the company Agilent Technologies, or similar devices.

As has been emphasized, the method of the invention makes it possible to separate the constituents of numerous mixtures. Thus, the method of the invention can be carried out on any mixture suitable for separation by electrophoresis. The nature of the separating medium introduced in step (C) can vary to quite a large extent depending on the exact nature of the constituents of the mixture M and of the constituents of the fraction F that is separated in step (C). However, in the most general case, a neutral compound, for example a neutral polymer, is advantageously involved.

Thus, according to a first variant, the mixture M separated into various constituents according to the method of the invention can be a mixture containing macromolecules carrying electrical charges, for example a mixture M comprising proteins, peptides, nucleic acids such as DNA or RNA, polysaccharides, humic acids, fluvic acids, or alternatively synthetic polymers. The mixture can thus, for example, be a biological medium (containing macromolecules (proteins, DNA, polysaccharides, etc.) and molecules of smaller size (in particular peptides)), or alternatively a medium derived from a polymerization reaction. The method of the invention is particularly suitable for separating a mixture M of proteins.

According to this specific variant, step (A) is advantageously an electrophoresis step without separating medium ("in a free medium"), allowing separation of the macromolecules according to their charge/mass ratio, the separating medium MS introduced in step (C) then preferably being a solution of a noncharged polymer suitable for separation of the compounds present in the isolated fraction F according to their mass. Alternatively, step (A) can advantageously be an "isoelectric focusing" electrophoresis step, for example of the type of that described in Recent advances in capillary isoelectric focusing, K. Shimura, Electrophoresis, 2002, 23, 3847-3857, consisting in separating the constituents of the mixture M according to their isoelectric point by creating a pH gradient in the capillary. Such an isoelectric focusing separation step is in particular suitable when the medium M contains proteins and/or peptides.

The polymers that can be used in the solutions for separation of the compounds of the fraction F according to their mass can in particular be selected from the high molecular weight polymers used in conventional capillary electrophoresis for this type of separation according to mass. These polymers are, as a general rule, water-soluble neutral polymers having a molecular mass of advantageously greater than or equal to $10^4$ g/mol, and preferably of at least $10^5$ g/mol. When infrared or ultraviolet detection of the constituents to be separated in the capillary is carried out, which in practice is almost always the case, it is also preferable for the separating medium MS to be transparent at the wavelength used for the detection.

To carry out a separation according to mass in step (C), it is thus possible to use, as separating medium MS, a solution (generally aqueous) of hydroxyethylated cellulose (hydroxyethylcellulose) or a solution of another suitable modified cellulose (such as hydroxypropylcellulose or hydroxypropylmethylcellulose), or alternatively a solution of other suitable polymers, such as, in particular, solutions of dextran, of pullulan, of polyoxyethylene, of polyacrylamide or of poly(vinyl alcohol). Whatever the nature of the polymer used, the concentration of polymer in the MS medium is advantageously at least equal to 0.5 g/l, and most commonly at least equal to 1 g/l, this concentration generally being less than 200 g/l, preferably less than or equal to 100 g/l. Thus, this concentration can typically be between 1 and 50 g/l. More generally, it is often advantageous for the concentration of polymer to be sufficient for the polymers to form, in the MS medium, an entangled structure, in particular so as to allow separation according to the pronounced mass during step (C). In particular, the MS medium used can be a solution of hydroxyethylated cellulose (hydroxyethyl-cellulose), having a molecular mass greater than or equal to $10^5$ g/mol (for example, between $2 \times 10^5$ and $5 \times 10^5$ g/mol, and typically of the order of $2.5 \times 10^5$ g/mol) and a concentration of greater than or equal to 0.3 g/l (for example, between 4 and 6 g/l, and typically of the order of 5 g/l).

According to a second variant that may be contemplated, the mixture M separated into various constituents according to the method of the invention is a mixture of charged molecules having a molar mass of less than 1000 g/mol, such as, for example, peptides, amino acids, acidic molecules or their salts (carboxylates, sulfonates, sulfates, phosphates, etc.) or basic molecules (in particular, amines or their corresponding ammonium salts), or alternatively active ingredients.

According to this second variant, step (A) is advantageously an electrophoresis step without separating medium, allowing separation of the macromolecules according to their charge/mass ratio. The separating medium introduced in step (C) can vary to a large extent, and is then advantageously:

a solution comprising noncharged chiral compounds, for example cyclodextrins (or cyclodextrin derivatives such as substituted cyclodextrins), crown ethers, macrocyclic antibiotics such as vancomycin, chiral polysaccharides such as maltodextrins or alternatively neutral chiral micelles (for example, cholates or deoxycholates). In this case, in step (C), separation of the compounds present in the isolated fraction F according to their affinity with respect to the chiral compound is carried out, which results in separation of the compounds according to their own chirality;

a solution of a nonionic or, optionally, zwitterionic surfactant used under pH conditions in which it does not carry a charge, advantageously at a concentration greater than its critical micellar concentration, as a result of which, in step (C), separation of the compounds present in the isolated fraction F according to their hydrophobic nature is carried out. By way of surfactants that can be used in this context, mention may e.g. be made of neutral surfactants with a polyoxyethylene head (such as those sold under the generic name "Brij") or the zwitterionic surfactants such as DAPS (N-dodecyl-N,N-dimethyl-3-ammonio-1-propanesulfonate).

More generally, any medium that is suitable as a separating medium can be introduced into the capillary during step (C), provided that it can be introduced into the capillary by means of an electroosmotic flow and that it has a migration speed that is faster than that of the fraction F. To this effect, generally, the separating medium MS introduced during step (C) advantageously comprises one or more noncharged compounds.

As emphasized above, the separation method of the present invention is a method which is both simple to carry out and effective, and which, in most cases, makes it possible to obtain a particularly resolvent separation of constituents of the mixture M.

The method of the invention also has the advantage of being carried out in a single capillary, which makes it possible to recover the separated compounds at the outlet of said capillary, as in the case of a conventional capillary electrophoresis. This feature makes it especially possible to contemplate an analysis of the separated constituents obtained at the end of step (C). To this end, following the separation in step (C), the compounds in separated form are injected from the capillary to an analytical device, such as a mass spectrometer (quadrupole, ion trap, time of flight), or alternatively a conductimetric or electrochemical detector (on-line injection from the capillary to another analytical device). This particular use of the method constitutes another specific subject-matter of the present invention.

BRIEF DESCRIPTION OF THE DRAWING FIGURES

Various aspects and advantages of the method will emerge even more explicitly in view of the examples below, and in view of the attached figures, wherein.

DETAILED DESCRIPTION OF THE INVENTION

EXAMPLE 1

Figure 1:
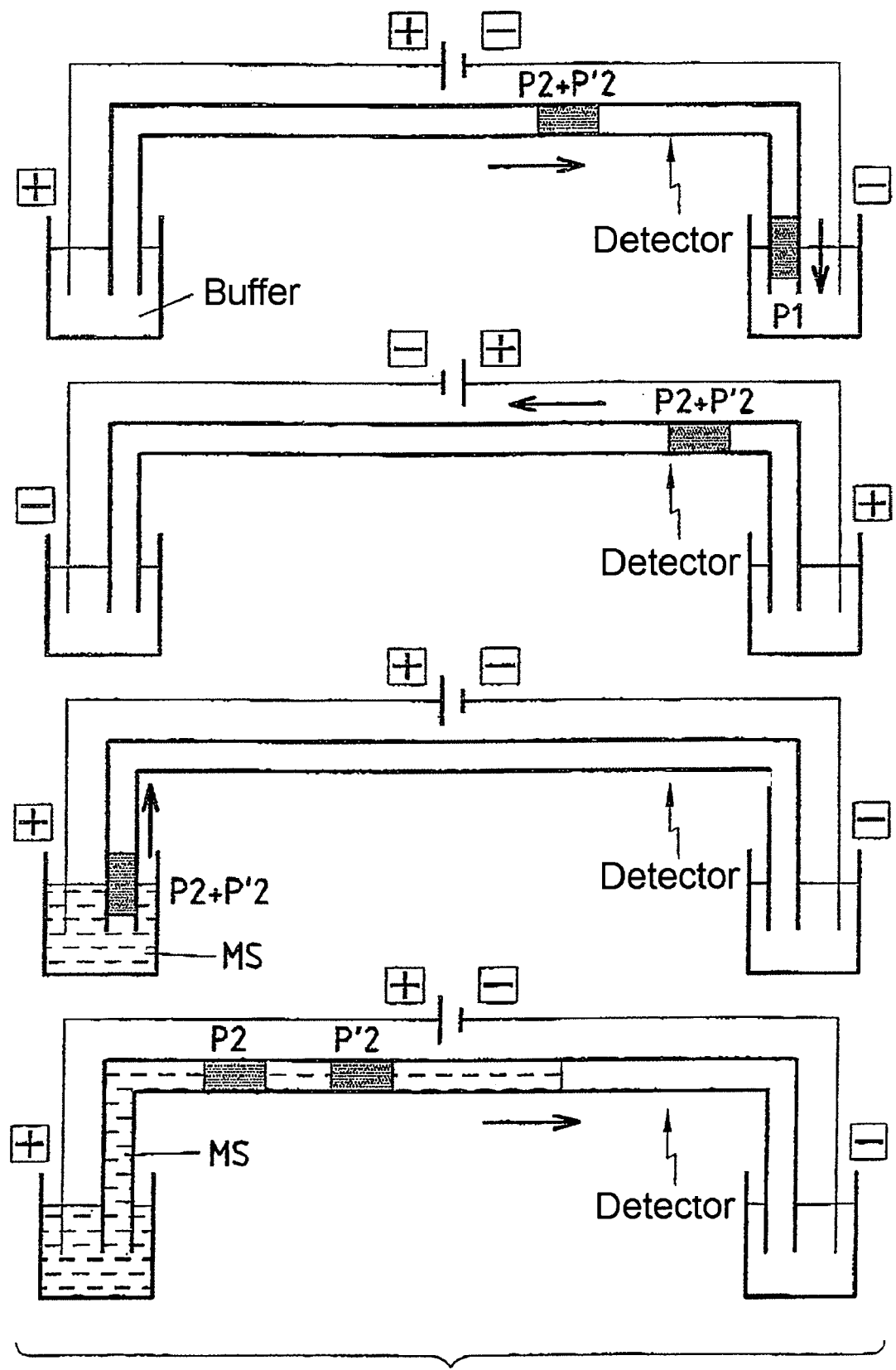
FIG. 1 is a diagram illustrating the separation carried out in Example 1.
Figure 2:
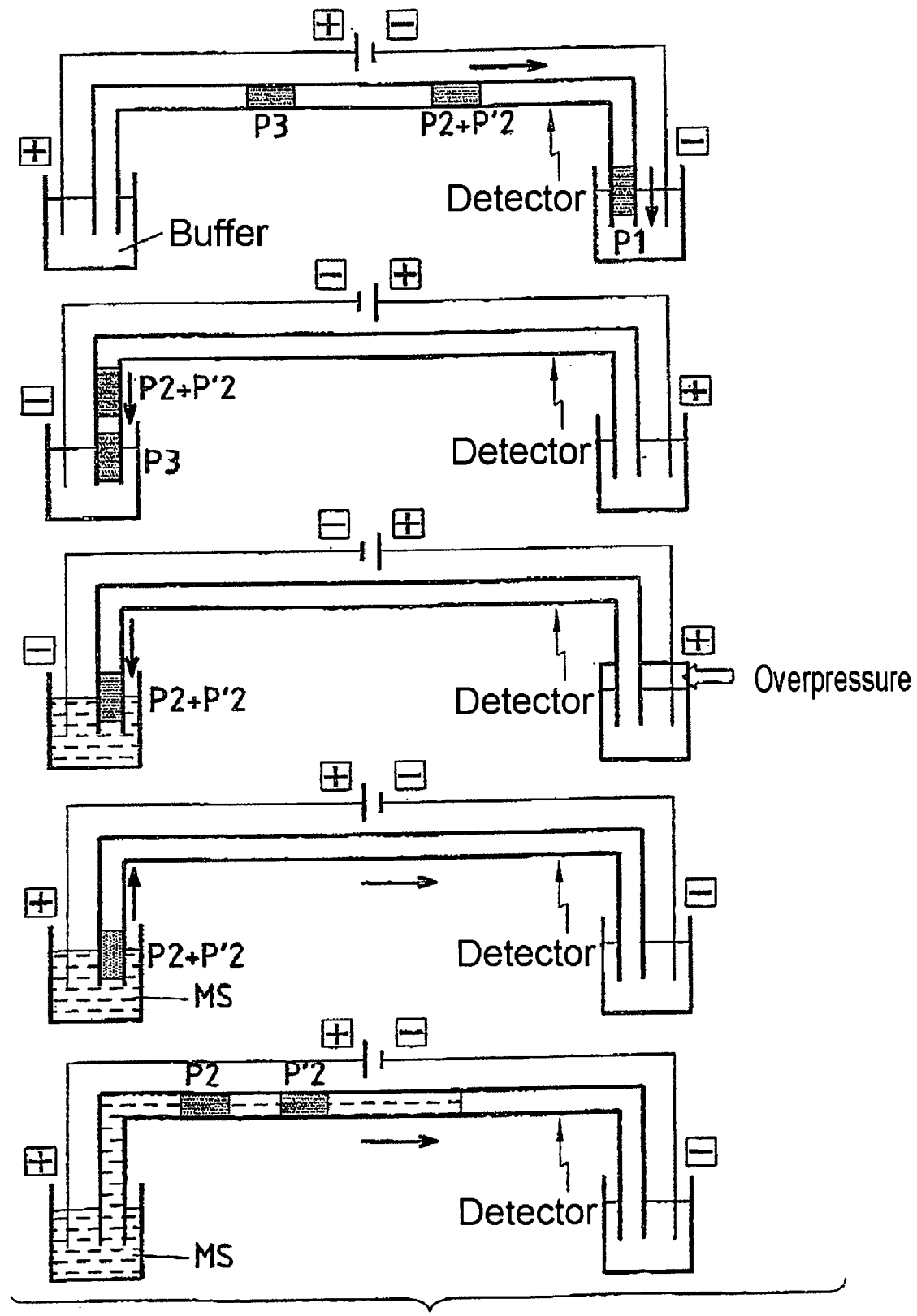
FIG. 2 is a diagram illustrating the separation performed in Example 2.

Two-Dimensional Separation, in a Single Capillary, of a Mixture of Three Anionic Polymers (Anionic Polyelectrolytes)

In this example, a virgin silica capillary, having an internal diameter of 50 microns and a length equal to 30 cm, was used. In order to follow the progression of the separation in the capillary, a detector was placed 20 cm from the capillary inlet.

A mixture of the following three polymers was separated according to the method of the invention:

polymer P1: random copolymer of acrylamide (90% by mass) and of 2-acrylamido-2-methyl-propanesulfonate (10% by mass) having a charge fraction of 10% and a molar mass of $2 \times 10^5$ g/mol;

polymer P2: polystyrene sulfonate (charge fraction 100%) having a molar mass equal to $3.33 \times 10^5$ g/mol (polymolecularity index less than 1.2);

polymer P'2: polystyrene sulfonate (charge fraction 100%) having a molar mass equal to $1.45 \times 10^5$ g/mol (polymolecularity index less than 1.2).

The mixture of the polymers P1, P2 and P'2 that was tested is an aqueous solution of the polymers, with a concentration of polymer P1 of 5 g/l, a concentration of polymer P2 of 0.5 g/l, and a concentration of polymer P'2 of 0.5 g/l.

1.1: Electrophoretic Separation of the Polymers According to Their Charge Fraction (First Dimension of Separation)

The polymer P1, firstly, and the polymers P2 and P'2, secondly, have different charge fractions which allow them to be separated by electrophoresis in a free medium.

To do this, the capillary was filled with a separating buffer (80 mM borate buffer of pH 9.2), injected under pressure into the capillary. The capillary was purged for 5 minutes with the borate buffer.

4 nl (nanoliters) of the solution of the polymers P1, P2 and P'2 were subsequently injected into the capillary, hydrodynamically (under a pressure of 0.3 psi for 3 seconds).

A potential difference of +20 kV was subsequently applied, between the inlet and the outlet of the capillary, immersed in borate buffer solutions, so as to separate the polymers according to their charge fraction, by electrophoresis.

Under the conditions of the electrophoresis carried out, the silica surface of the capillary is negatively charged, which induces a cationic electroosmotic flow directed from the inlet to the outlet of the capillary. The anionic polymers consequently migrate at an electroosmotic counter-flow. Consequently, the least charged polymer, i.e. the polymer P1, has a migration speed that is faster than that of the other two polyelectrolytes P2 and P'2.

The appearance of a first peak (head peak) corresponding to the polymer P1 was observed at the detector, followed by a second peak (tail peak) corresponding to the mixture of the polymers P2 and P'2.

1.2: Elimination of the Polymer P1 (Head Peak)

The potential difference of +20 kV applied in step 1.1 was maintained so as to allow the polymer P1 (head peak) to leave the capillary and to keep the polyelectrolytes P2 and P'2 (tail peak) in the capillary.

In order to carry out this elimination, the time T (of the order of a little less than 13 minutes) taken by the polymer P1 to travel the first 20 centimeters of the capillary (from the inlet to the detector) was measured and, starting from the moment at which the polymer P1 was detected, it was allowed to migrate for the time T/2 (required to travel the remaining 10 centimeters), plus a few tens of seconds in order to be sure that all the polymer P1 has left the capillary. In practice, the migration was allowed to take place for 1.7 minutes.

In summary, during steps 1.1 and 1.2, the potential difference of +20 kV between the inlet and the outlet of the capillary was therefore maintained for 3 minutes.

1.3: Migration of the Isolated Polymers P2 and P'2 (Tail Peak) Toward the Inlet of the Capillary The polarity between the inlet and the outlet of the capillary was reversed (imposed potential difference of −20 kV), as a result of which the direction of migration of the compounds was reversed. The polymers P2 and P'2 isolated in the capillary therefore migrated toward the inlet of the capillary. The return of these polymers, still in the form of a single peak, was observed at the detector, and the disappearance of the peak corresponding to the polymer P1 was verified.

The potential difference of −20 kV was maintained for the total amount of time taken by the migration at +20 kV carried out in steps 1.1 and 1.2, minus a few seconds so as to be sure not to cause the compounds P2 and P'2 to exit via the inlet of the capillary. The potential difference of −20 kV was thus maintained for 2 minutes and 45 seconds.

1.4: Introduction of a Separating Medium and Separation of the Polymers P2 and P'2 in the Capillary (Second Dimension of Separation)

The capillary inlet was immersed in a solution consisting of an 80 mM/l borate buffer of pH equal to 9.2 and comprising 5 g/l of hydroxyethylcellulose having a molar mass equal to $2.5 \times 10^5$ g/mol.

A potential difference of +6 kV was applied between the inlet of the capillary immersed in the solution of hydroxyethylcellulose, and the outlet immersed in a borate buffer (80 mM aqueous solution of pH 9.2, without polymer).

An electroosmotic flow was thus created, entraining the hydroxyethylcellulose into the capillary with an apparent speed greater than that of the polyelectrolytes P2 and P'2. The hydroxyethylcellulose thus caught up with the polymers P2 and P'2 in the capillary, and separation of the polymers P2 and P'2 was obtained according to their size.

Separation of the polymers P2 and P'2 according to their molar mass under the new electrophoresis conditions was observed at the detector.

EXAMPLE 2

Two-Dimensional Separation, in a Single Capillary, of a Mixture of Four Anionic Compounds (3 Anionic Polymers and an Anionic Molecule of Smaller Size)

In this example, a virgin silica capillary having an internal diameter of 25 microns and a length equal to 30 cm was used. In order to follow the progress of the separation in the capillary, a detector was placed 20 cm from the capillary inlet, as in Example 1.

A mixture of the following four compounds was separated according to the method of the invention:
  the polymer P1 of Example 1;
  the polymer P2 of Example 1;
  the polymer P'2 of Example 1; and
  a compound P3: orthophthalic acid, ionized in the form of orthophthalate anions (under the separating conditions, the pH is 9.2).

The mixture of the compounds P1, P2, P'2 and P3 that was tested is an aqueous solution of these compounds, with a concentration of polymer P1 of 5 g/l, a concentration of polymer P2 of 0.5 g/l, a concentration of polymer P'2 of 0.5 g/l, and a concentration of compound P3 of 0.5 g/l.

2.1: Electrophoretic Separation of the Compounds of the Mixture (First Dimension of Separation)

The capillary was filled with a separating buffer (90 mM borate buffer, of pH 9.2), injected under pressure into the capillary. The capillary was purged for 5 minutes with the borate buffer.

4 nl (nanoliters) of the solution of the polymers P1, P2, P'2 and P3 were subsequently injected into the capillary, hydrodynamically (under a pressure of 0.3 psi for 12 seconds).

A potential difference of +20 kV was subsequently applied, between the inlet and the outlet of the capillary, immersed in buffer solutions, so as to separate the compounds by electrophoresis.

Under the conditions of the electrophoresis carried out, the appearance of a first peak (head peak) corresponding to the polymer P1 was observed, at the detector, followed by a second peak (core peak) corresponding to the mixture of the polymers P2 and P'2, and then a final peak (tail peak) corresponding to the compound P3.

2.2: Elimination of the Polymer P1 (Head Peak)

The potential difference of +20 kV applied in step 2.1 was maintained so as to allow the polymer P1 (head peak) to exit the capillary and to conserve in the capillary the polyelectrolytes P2 and P'2 (core peak) and the compound P3 (tail peak).

In order to carry out this elimination, as in Example 1, the time T taken by the polymer P1 to travel the first 20 centimeters of the capillary (from the inlet to the detector) was measured and, starting from the moment at which the polymer P1 was detected, it was allowed to migrate for a time T/2, plus a few tens of seconds so as to be sure that all the polymer P1 had left the capillary.

In summary, during steps 2.1 and 2.2, the potential difference of +20 kV between the inlet and the outlet of the capillary was maintained for 4.7 minutes.

2.3: Elimination of the Compound P3 (Tail Peak) and Migration of the Polymers P2 and P'2 (Core Peak) Toward the Inlet of the Capillary The polarity between the inlet and the outlet of the capillary was reversed (imposed potential difference of −20 kV), as a result of which the direction of migration of the compounds was reversed. This potential difference was applied for 3 minutes.

The return of the polymers P2 and P'2, still in the form of a single peak, and of the tail peak corresponding to the compound P3, was observed at the detector. The disappearance of the peak corresponding to the polymer P1 was verified.

This potential difference of −20 kV was subsequently applied for a continuing 1.4 minutes while at the same time applying an overpressure of 0.3 psi at the outlet of the capillary.

These steps make it possible to evacuate the compound P3 from the capillary (via the inlet) and to migrate the polymers P2 and P'2 toward the inlet of the capillary, without causing them to exit it.

2.4: Introduction of a Separating Medium and Separation of the Polymers P2 and P'2 in the Capillary (Second Dimension of Separation)

The inlet of the capillary containing the polymers P2 and P'2 isolated above was immersed in a 90 mM/l borate buffer of pH 9.2, containing 5 g/l of hydroxyethyl-cellulose having a molar mass equal to $2.5 \times 10^5$ g/mol.

A potential difference of +6 kV was applied between the inlet of the capillary immersed in the hydroxyethyl-cellulose solution and the outlet immersed in a borate buffer (80 mM aqueous solution of pH 9.2, without polymer).

An electroosmotic flow was thus created, entraining the hydroxyethylcellulose into the capillary with an apparent speed greater than that of the polyelectrolytes P2 and P'2 (migration of the polyelectrolytes in the counter-electroosmotic mode). The hydroxyethylcellulose thus caught up with the polymers P2 and P'2 in the capillary, and separation of the polymers P2 and P'2 was obtained according to their size.

At the detector, it has been observed a separation of the polymers P2 and P'2 according to their molar mass under the new electrophoresis conditions.

The invention claimed is:
1. A method for separating the constituents of a mixture M comprising electrically charged compounds, implementing a capillary electrophoresis in a single capillary, wherein said method comprises:
  (A) introducing and migrating the compounds of the mixture M in said capillary according by the capillary electrophoresis, so as to produce a separation of the compounds of the mixture M in the capillary according to their migration speed under the conditions of step (A);
  (B) isolating in the capillary a fraction F of the compounds separated in step (A), the isolating consisting of at least one of the following steps:
    (B.1) evacuating out of the capillary a part of the compounds having fastest migration speeds under the electrophoresis conditions of step (A), by allowing these compounds to migrate at an outlet of the capillary; and/or
    (B.2) evacuating out of the capillary a part of the compounds having slowest migration speeds under the electrophoresis conditions of step (A), by migrating these compounds toward an inlet of the capillary; and
  (C) under an effect of a potential difference applied between the inlet and the outlet of the capillary, introducing, into the capillary containing the isolated fraction

F, a separating medium MS having a migration speed greater than that of the compounds of said fraction F, such that said separating medium MS catches up with said fraction F in the capillary, and modifies the electrophoresis conditions for this fraction, and maintaining the potential difference until there is separation of the compounds included in the fraction F as a function of their migration speed under the new electrophoresis conditions obtained.

2. The method of claim 1, wherein step(B) consists of carrying out step (B.2) without carrying out step (B.1), the isolated fraction F in the capillary then being a head fraction.

3. The method of claim 2, where the head fraction F comprises the compounds of a head peak that can be observed on an electropherogram of the electrophoresis of step (A).

4. The method of claim 2, wherein step (B.2) comprises applying an overpressure at the outlet of the capillary, until the compounds that are not part of the head fraction F to be isolated are made to exit via the inlet of the capillary.

5. The method of claim 2, wherein step (B.2) comprises:
   (i) applying, between the inlet and the outlet of the capillary, a potential difference of opposite polarity to that of step (A), taking care not to recombine the fraction F to be isolated with the other compounds separated from the mixture M; then
   (ii) applying an overpressure at the outlet of the capillary until the compounds that are not part of the head fraction F to be isolated are made to exit via the inlet of the capillary.

6. The method of claim 1, wherein step (B) consists of carrying out step (B.1) so as to evacuate a head fraction, and then step (B.2) so as to evacuate a tail fraction, the isolated fraction F in the capillary then being a core fraction.

7. The method of claim 6, where the core fraction F comprises compounds of one of the peaks between a tail peak and a head peak that can be observed on an electropherogram of the electrophoresis of step (A).

8. The method of claim 6, wherein step (B.2) comprises applying an overpressure at the outlet of the capillary, until the compounds that are not part of the head fraction F to be isolated are made to exit via the inlet of the capillary.

9. The method of claim 6, wherein step (B.2) comprises:
   (i) applying, between the inlet and the outlet of the capillary, a potential difference of opposite polarity to that of step (A), taking care not to recombine the fraction F to be isolated with the other compounds separated from the mixture M; then
   (ii) applying an overpressure at the outlet of the capillary until the compounds that are not part of the head fraction F to be isolated are made to exit via the inlet of the capillary.

10. The method of claim 1, in which step (B) consists of carrying out step (B.1) without carrying out step (B.2), the isolated fraction F in the capillary then being a tail fraction.

11. The method of claim 10, where the tail fraction F comprises compounds of a tail peak that can be observed on an electropherogram of the electrophoresis of step (A).

12. The method of claim 1, wherein, prior to the introduction of the separating medium of step (C), the isolated fraction F in the capillary is migrated toward the inlet of the capillary.

13. The method of claim 12, wherein the migration of the isolated fraction F in the capillary toward the inlet of the capillary is induced by applying an overpressure at the outlet of the capillary.

14. The method of claim 12, wherein the migration of the isolated fraction F in the capillary toward the inlet of the capillary is induced by applying, between the inlet and the outlet of the capillary, a potential difference of opposite polarity to that of step (A).

15. The method of claim 1, wherein the capillary used in steps (A) to (C) is a capillary having an internal diameter of between 5 and 100 microns.

16. The method of claim 1, wherein the capillary used in steps (A) to (C) is a capillary having a length of less than 1 m.

17. The method of claim 1, where the mixture M is a mixture containing macromolecules carrying electrical charges.

18. The method of claim 17, wherein the mixture M comprises proteins, peptides, nucleic acids, polysaccharides, humic acids, fluvic acids or synthetic polymers.

19. The method of claim 18, wherein the mixture M is a mixture of proteins.

20. The method of claim 17, wherein step (A) is an electrophoresis step without separating medium, referred to as "in a free medium", allowing separation of the macromolecules according to the charge/mass ratio, and in that the separating medium introduced in step (C) is a solution of a noncharged polymer suitable for separation of the compounds present in the isolated fraction F according to their mass.

21. The method of claim 20, wherein the separating medium introduced in step (C) is a solution of hydroxyethylated cellulose, of a hydroxy-propylcellulose, of dextran, of pullulan, of polyoxyethylene, of polyacrylamide or of poly (vinyl alcohol).

22. The method of claim 1, where the mixture M is a mixture of charged molecules having a molar mass of less than 1000 g/mol.

23. The method of claim 22, wherein step (A) is an electrophoresis step without separating medium, allowing separation of the macromolecules according to their charge/mass ratio, and in that the separating medium introduced in step (C) is a solution of a noncharged chiral compound, as a result of which, in step (C), separation of the compounds present in the isolated fraction F according to their affinity with respect to the chiral compound is carried out.

24. The method of claim 22, wherein step (A) is an electrophoresis step without separating medium, allowing separation of the macromolecules according to their charge/mass ratio, and in that the separating medium introduced in step (C) is a solution of a surfactant, as a result of which, in step (C), separation of the compounds present in the isolated fraction F according to their hydrophobic nature is carried out.

25. The method of claim 1, wherein the separated compounds obtained at the end of step (C) are injected from the capillary to an analytical device, for analyzing said separated constituents.

* * * * *